United States Patent [19]

Fischer et al.

[11] Patent Number: 5,840,950
[45] Date of Patent: Nov. 24, 1998

[54] PROCESS FOR CONVERTING THE ACHIRAL MESO FORM OR THE RACEMATE OF AN ANSA-METALLOCENE COMPLEX OR MIXTURES THEREOF INTO ONE OF ITS ENANTIOMERS

[75] Inventors: David Fischer, Gönnheim; Franz Langhauser, Bad Dürkheim; Rainer Stürmer, Roedersheim; Jürgen Kerth, Carlsberg; Günther Schweier, Friedelsheim, all of Germany; Hans-Herbert Brintzinger, Taegerswilen, Switzerland; Katrin Schmidt, Constance, Germany

[73] Assignee: BASF Aktiengesellschaft, Ludwigshafen, Germany

[21] Appl. No.: 981,638

[22] PCT Filed: Jan. 7, 1996

[86] PCT No.: PCT/EP96/02869

§ 371 Date: Jan. 8, 1998

§ 102(e) Date: Jan. 8, 1998

[87] PCT Pub. No.: WO97/03081

PCT Pub. Date: Jan. 30, 1997

[30] Foreign Application Priority Data

Jul. 11, 1995 [DE] Germany .................. 195 25 184.9

[51] Int. Cl.⁶ .............. C07F 17/00; C07F 9/00; C07F 5/00

[52] U.S. Cl. ............. 556/11; 556/7; 556/12; 556/13; 556/21; 556/28; 556/27; 556/43; 556/53; 556/54; 502/103; 502/117; 502/152; 502/162; 526/160; 526/943

[58] Field of Search .................. 556/11, 12, 21, 556/13, 7, 27, 28, 43, 53, 54; 502/152, 162, 103, 117; 526/943, 160

[56] References Cited

FOREIGN PATENT DOCUMENTS

92/09545  6/1992  WIPO.

OTHER PUBLICATIONS

Schmidt et al., Organometallics, vol. 16, No. 8, pp. 1724–1728, 1997.
J. of Organic Chem. vol. 54, 1989, pp. 4154–4158.
Makromol. Chem. Rapid Comm, vol. 8, 1987, S.305–310.
W.Kaminsky et al., Angew.Chem.101(1989), pp. 1304–1306.
Huttenloch et al.,Organometallics 11,1992, pp. 3600–3607.
Rheingold et al., Organometallics 11, 1992, pp. 1869–1876.
Wiesenfeldt et al., J. of Organomet. Chem.,369,1989, pp. 359–370.
Brintzinger et al. J. of Organomet. Chem, 232, 1982, pp. 233–247.
J. Am. Chem. Soc. vol. 114, 1992, pp. 9300–9304.
J. of Organomet. Chem. 342 (1988), 21–29.

*Primary Examiner*—Porfirio Nazario-Gonzalez
*Attorney, Agent, or Firm*—Keil & Weinkauf

[57] ABSTRACT

In a process for converting the achiral meso form or the racemate of an ansa-metallocene complex or a mixture thereof into one of its enantiomers, the conversion is carried out photochemically in the presence of an enantiomerically pure auxiliary reagent.

9 Claims, No Drawings

PROCESS FOR CONVERTING THE ACHIRAL MESO FORM OR THE RACEMATE OF AN ANSA-METALLOCENE COMPLEX OR MIXTURES THEREOF INTO ONE OF ITS ENANTIOMERS

The present invention relates to a process for converting the achiral meso form or the racemate of an ansa-metallocene complex or a mixture thereof into one of its enantiomers.

Apart from the stereospecific polymerization of olefins, enantioselective organic synthesis increasingly offers interesting possible uses of chiral ansa-metallocene complexes of metals of transition group IV of the Periodic Table of the Elements. Examples which may be mentioned here are enantioselective hydrogenations of prochiral substrates, for example prochiral olefins as described in R. Waymouth, P. Pino, J. Am. Chem. Soc. 112 (1990), p. 4911–4914, or prochiral ketones, imines and oximes as described in WO 92/9545.

Mention may also be made of the preparation of optically active alkenes by enantioselective oligomerization as described in W. Kaminsky et al., Angew. Chem. 101 (1989), p. 1304–1306, and also the enantioselective cyclopolymerization of 1,5-hexadienes as described in R. Waymouth, G. Coates, J. Am. Chem. Soc. 113 (1991), p. 6270–6271.

Unlike stereospecific olefin polymerization, all applications in enantioselective organic synthesis require the use of an enantiomerically pure ansa-metallocene complex, ie. the meso form first has to be removed from the mixture of diastereomers (rac and meso form) obtained in the metallocene synthesis and the remaining rac form has to be subjected to resolution of the enantiomers. Since both the meso form and one of the two enantiomers have to be discarded, the yield of the enantiomerically pure ansa-metallocene complex is very low.

Diastereoselective or even enantioselective syntheses of chiral ansa-metallocene complexes are known for only very few, specific ligand systems which are described, for example, in Brintzinger et al., organometallics 11 (1992), p. 3600–3607 and in Rhein-gold et al., Organometallics 11 (1992), p. 1869–1876.

It is an object of the present invention to provide a process for the quantitative conversion of the meso form or the racemate of an ansa-metallocene complex or a mixture thereof into one of its enantiomers. This conversion should be simple in process terms and inexpensive.

We have found that this object is achieved by a process for converting the achiral meso form or the racemate of an ansa-metallocene complex or a mixture thereof into one of its enantiomers wherein the conversion is carried out photochemically in the presence of an enantiomerically pure auxiliary reagent.

The terms "meso form", "racemate" and thus also "enantiomer" in the context of ansa-metallocene complexes are known and described, for example, in Rheingold et al., Organometallics 11 (1992), p. 1869–1876.

For the purposes of the present invention, the term "enantiomerically pure" means that at least 90% of a compound is present in the form of one enantiomer.

Particularly suitable ansa-metallocene complexes which can be used in the process of the present invention are those of the formula I

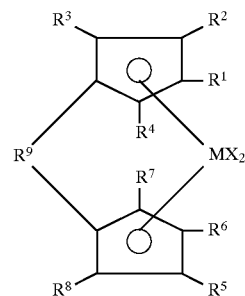

where the substituents and indices have the following meanings:
M is titanium, zirconium, hafnium, vanadium, niobium or tantalum,
X is fluorine, chlorine, bromine, iodine, hydrogen, $C_1$–$C_{10}$-alkyl, $C_6$–$C_{15}$-aryl or —$OR^{10}$,
where
$R^{10}$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical,
$R^1$ to $R^8$ are hydrogen, $C_1$–$C_{10}$-alkyl, 5- to 7-membered cycloalkyl which may in turn bear a $C_1$–$C_{10}$-alkyl group as substituent, $C_6$–$C_{15}$-aryl or arylalkyl, where two adjacent radicals may also together form a cyclic group having from 4 to 15 carbon atoms, or $Si(R^{11})_3$ where
$R^{11}$ is $C_1$–$C_{10}$-alkyl, $C_6$–$C_{15}$-aryl or $C_3$–$C_{10}$-cycloalkyl,
$R^9$ is

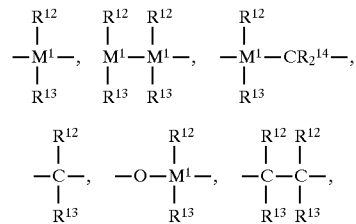

$=BR^{12}$, $=AlR^{12}$, —Ge—, —Sn—, —O—, —S—, $=SO$, $=SO_2$, $NR^{12}$, $=CO$, $=PR^{12}$ or $=P(O)R^{12}$, where
$R^{12}$, $R^{13}$ and $R^{14}$ are identical or different and are hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl or $C_7$–$C_{40}$-alkylaryl or $R^{12}$ and $R^{13}$ or $R^{12}$ and $R^{14}$ in each case together with the atoms connecting them form a ring, and
$M^1$ is silicon, germanium or tin.

Particularly suitable ansa-metallocene complexes are those of the formula I in which
M is titanium, zirconium or hafnium,
X is chlorine or $C_1$–$C_6$-alkyl,
$R^1$ to $R^8$ are hydrogen, $C_1$–$C_6$-alkyl, $C_1$–$C_{12}$-aryl or two adjacent radicals together form a cyclic group having from 4 to 15, in particular from 8 to 12, carbon atoms and $M^1$ is silicon.

Preference is given to ansa-metallocene complexes of the formula I which are substituted in the 2 position of the cyclopentadienyl rings, ie. $R^4$ and $R^7$ in the formula I are different from hydrogen and are, in particular, methyl, ethyl, n-propyl, iso-propyl, n-butyl, tert-butyl or phenyl.

Furthermore, preference is given to those ansa-metallocene complexes which are silyl-bridged, ie. $M^1$ is silicon.

Examples of particularly suitable ansa-metallocene complexes are, inter alia:

dimethylsilanediylbis(2-methyl-4-methyl-1-cyclopentadienyl)zirconium dichloride
dimethylsilanediylbis(2-methyl-4-ethyl-1-cyclopentadienyl)zirconium dichloride
dimethylsilanediylbis(2-methyl-4-propyl-1-cyclopentadienyl)zirconium dichloride
dimethylsilanediylbis(2-methyl-4-butyl-1-cyclopentadienyl)zirconium dichloride
dimethylsilanediylbis(2-methyl-4-i-propyl-1-cyclopentadienyl)zirconium dichloride
dimethylsilanediylbis(2-methyl-4-i-butyl-1-cyclopentadienyl)zirconium dichloride
dimethylsilanediylbis(2-methyl-4-t-butyl-1-cyclopentadienyl)zirconium dichloride
dimethylsilanediylbis(2-methyl-4-trimethylsilyl-1-cyclopentadienyl)zirconium dichloride
dimethylsilanediylbis(2-methyl-4-phenyl-1-cyclopentadienyl)zirconium dichloride
dimethylsilanediylbis(2-ethyl-4-methyl-1-cyclopentadienyl)zirconium dichloride
dimethylsilanediylbis(2-ethyl-4-ethyl-1-cyclopentadienyl)zirconium dichloride
dimethylsilanediylbis(2-ethyl-4-propyl-1-cyclopentadienyl)zirconium dichloride
dimethylsilanediylbis(2-ethyl-4-butyl-1-cyclopentadienyl)zirconium dichloride
dimethylsilanediylbis(2-ethyl-4-i-propyl-1-cyclopentadienyl)zirconium dichloride
dimethylsilanediylbis(2-ethyl-4-i-butyl-1-cyclopentadienyl)zirconium dichloride
dimethylsilanediylbis(2-ethyl-4-t-butyl-1-cyclopentadienyl)zirconium dichloride
dimethylsilanediylbis(2-ethyl-4-trimethylsilyl-1-cyclopentadienyl)zirconium dichloride
dimethylsilanediylbis(2-ethyl-4-phenyl-1-cyclopentadienyl)zirconium dichloride
dimethylsilanediylbis(2-propyl-4-methyl-1-cyclopentadienyl)zirconium dichloride
dimethylsilanediylbis(2-propyl-4-ethyl-1-cyclopentadienyl)zirconium dichloride
dimethylsilanediylbis(2-propyl-4-propyl-1-cyclopentadienyl)zirconium dichloride
dimethylsilanediylbis(2-propyl-4-butyl-1-cyclopentadienyl)zirconium dichloride
dimethylsilanediylbis(2-propyl-4-i-propyl-1-cyclopentadienyl)zirconium dichloride
dimethylsilanediylbis(2-propyl-4-i-butyl-1-cyclopentadienyl)zirconium dichloride
dimethylsilanediylbis(2-propyl-4-t-butyl-1-cyclopentadienyl)zirconium dichloride
dimethylsilanediylbis(2-propyl-4-trimethylsilyl-1-cyclopentadienyl)zirconium dichloride
dimethylsilanediylbis(2-propyl-4-phenyl-1-cyclopentadienyl)zirconium dichloride
dimethylsilanediylbis(2-butyl-4-methyl-1-cyclopentadienyl)zirconium dichloride
dimethylsilanediylbis(2-butyl-4-ethyl-1-cyclopentadienyl)zirconium dichloride
dimethylsilanediylbis(2-butyl-4-propyl-1-cyclopentadienyl)zirconium dichloride
dimethylsilanediylbis(2-butyl-4-butyl-1-cyclopentadienyl)zirconium dichloride
dimethylsilanediylbis(2-butyl-4-i-propyl-1-cyclopentadienyl)zirconium dichloride
dimethylsilanediylbis(2-butyl-4-i-butyl-1-cyclopentadienyl)zirconium dichloride
dimethylsilanediylbis(2-butyl-4-t-butyl-1-cyclopentadienyl)zirconium dichloride
dimethylsilanediylbis(2-butyl-4-trimethylsilyl-1-cyclopentadienyl)zirconium dichloride
dimethylsilanediylbis(2-butyl-4-phenyl-1-cyclopentadienyl)zirconium dichloride
dimethylsilanediylbis(2-i-propyl-4-methyl-1-cyclopentadienyl)zirconium dichloride
dimethylsilanediylbis(2-i-propyl-4-ethyl-1-cyclopentadienyl)zirconium dichloride
dimethylsilanediylbis(2-i-propyl-4-propyl-1-cyclopentadienyl)zirconium dichloride
dimethylsilanediylbis(2-i-propyl-4-butyl-1-cyclopentadienyl)zirconium dichloride
dimethylsilanediylbis(2-i-propyl-4-i-propyl-1-cyclopentadienyl)zirconium dichloride
dimethylsilanediylbis(2-i-propyl-4-i-butyl-1-cyclopentadienyl)zirconium dichloride
dimethylsilanediylbis(2-i-propyl-4-t-butyl-1-cyclopentadienyl)zirconium dichloride.
dimethylsilanediylbis(2-i-propyl-4-trimethylsilyl-1-cyclopentadienyl)zirconium dichloride
dimethylsilanediylbis(2-i-propyl-4-phenyl-1-cyclopentadienyl)zirconium dichloride
dimethylsilanediylbis(2-t-butyl-4-methyl-1-cyclopentadienyl)zirconium dichloride
dimethylsilanediylbis(2-t-butyl-4-ethyl-1-cyclopentadienyl)zirconium dichloride
dimethylsilanediylbis(2-t-butyl-4-propyl-1-cyclopentadienyl)zirconium dichloride
dimethylsilanediylbis(2-t-butyl-4-butyl-1-cyclopentadienyl)zirconium dichloride
dimethylsilanediylbis(2-t-butyl-4-i-propyl-1-cyclopentadienyl)zirconium dichloride
dimethylsilanediylbis(2-t-butyl-4-i-butyl-1-cyclopentadienyl)zirconium dichloride
dimethylsilanediylbis(2-t-butyl-4-t-butyl-1-cyclopentadienyl)zirconium dichloride
dimethylsilanediylbis(2-t-butyl-4-trimethylsilyl-1-cyclopentadienyl)zirconium dichloride
dimethylsilanediylbis(2-t-butyl-4-phenyl-1-cyclopentadienyl)zirconium dichloride
dimethylsilanediylbis(2-trimethylsilyl-4-methyl-1-cyclopentadienyl)zirconium dichloride
dimethylsilanediylbis(2-trimethylsilyl-4-ethyl-1-cyclopentadienyl)zirconium dichloride
dimethylsilanediylbis(2-trimethylsilyl-4-propyl-1-cyclopentadienyl)zirconium dichloride
dimethylsilanediylbis(2-trimethylsilyl-4-butyl-1-cyclopentadienyl)zirconium dichloride
dimethylsilanediylbis(2-trimethylsilyl-4-i-propyl-1-cyclopentadienyl)zirconium dichloride
dimethylsilanediylbis(2-trimethylsilyl-4-i-butyl-1-cyclopentadienyl)zirconium dichloride
dimethylsilanediylbis(2-trimethylsilyl-4-t-butyl-1-cyclopentadienyl)zirconium dichloride
dimethylsilanediylbis(2-trimethylsilyl-4-trimethylsilyl-1-cyclopentadienyl)zirconium dichloride
dimethylsilanediylbis(2-trimethylsilyl-4-phenyl-1-cyclopentadienyl)zirconium dichloride
dimethylsilanediylbis(2-phenyl-4-methyl-1-cyclopentadienyl)zirconium dichloride
dimethylsilanediylbis(2-phenyl-4-ethyl-1-cyclopentadienyl)zirconium dichloride
dimethylsilanediylbis(2-phenyl-4-propyl-1-cyclopentadienyl)zirconium dichloride
dimethylsilanediylbis(2-phenyl-4-butyl-1-cyclopentadienyl)zirconium dichloride
dimethylsilanediylbis(2-phenyl-4-i-propyl-1-cyclopentadienyl)zirconium dichloride dimethylsilanediylbis(2-phenyl-4-i-butyl-1-cyclopentadienyl)zirconium dichloride
dimethylsilanediylbis(2-phenyl-4-t-butyl-1-cyclopentadienyl)zirconium dichloride
dimethylsilanediylbis(2-phenyl-4-trimethylsilyl-1-cyclopentadienyl)zirconium dichloride
dimethylsilanediylbis(2-phenyl-4-phenyl-1-cyclopentadienyl)zirconium dichloride
dimethylsilanediylbis(2-methyl-1-indenyl)zirconium dichloride
dimethylsilanediylbis(2-ethyl-1-indenyl)zirconium dichloride
dimethylsilanediylbis(2-propyl-1-indenyl)zirconium dichloride
dimethylsilanediylbis(2-butyl-1-indenyl)zirconium dichloride
dimethylsilanediylbis(2-i-propyl-1-indenyl)zirconium dichloride
dimethylsilanediylbis(2-t-butyl-1-indenyl)zirconium dichloride
dimethylsilanediylbis(2-trimethylsilyl-1-indenyl)zirconium dichloride
dimethylsilanediylbis(2-phenyl-1-indenyl)zirconium dichloride
dimethylsilanediylbis(2-methyl-4,5,6,7-tetrahydro-1-indenyl)zirconium dichloride
dimethylsilanediylbis(2-ethyl-4,5,6,7-tetrahydro-1-indenyl)zirconium dichloride
dimethylsilanediylbis(2-propyl-4,5,6,7-tetrahydro-1-indenyl)zirconium dichloride
dimethylsilanediylbis(2-butyl-4,5,6,7-tetrahydro-1-indenyl)zirconium dichloride
dimethylsilanediylbis(2-i-propyl-4,5,6,7-tetrahydro-1-indenyl)zirconium dichloride
dimethylsilanediylbis(2-t-butyl-4,5,6,7-tetrahydro-1-indenyl)zirconium dichloride
dimethylsilanediylbis(2-trimethylsilyl-4,5,6,7-tetrahydro-1-indenyl)zirconium dichloride
dimethylsilanediylbis(2-phenyl-4,5,6,7-tetrahydro-1-indenyl)zirconium dichloride
dimethylsilanediylbis (2-methyl-4,7-dimethyl-1-indenyl)zirconium dichloride
dimethylsilanediylbis(2-ethyl-4,7-dimethyl-1-indenyl)zirconium dichloride
dimethylsilanediylbis(2-propyl-4,7-dimethyl-1-indenyl)zirconium dichloride
dimethylsilanediylbis(2-butyl-4,7-dimethyl-1-indenyl)zirconium dichloride
dimethylsilanediylbis(2-i-propyl-4,7-dimethyl-1-indenyl)zirconium dichloride
dimethylsilanediylbis(2-t-butyl-4,7-dimethyl-1-indenyl)zirconium dichloride
dimethylsilanediylbis(2-trimethylsilyl-4,7-dimethyl-1-indenyl)zirconium dichloride
dimethylsilanediylbis(2-phenyl-4,7-dimethyl-1-indenyl)zirconium dichloride
dimethylsilanediylbis(2-methyl-4,6-di-i-propyl-1-indenyl)zirconium dichloride
dimethylsilanediylbis (2-ethyl-4,6-di-i-propyl-1-indenyl)zirconium dichloride
dimethylsilanediylbis(2-propyl-4,6-di-i-propyl-1-indenyl)zirconium dichloride
dimethylsilanediylbis(2-butyl-4,6-di-i-propyl-1-indenyl)zirconium dichloride
dimethylsilanediylbis(2-i-propyl-4,6-di-i-propyl-1-indenyl)zirconium dichloride
dimethylsilanediylbis(2-t-butyl-4,6-di-i-propyl-1-indenyl)zirconium dichloride
dimethylsilanediylbis(2-trimethylsilyl-4,6-di-i-propyl-1-indenyl)zirconium dichloride
dimethylsilanediylbis(2-phenyl-4,6-di-i-propyl-1-indenyl)zirconium dichloride
dimethylsilanediylbis(2-methyl-1-benzindenyl)zirconium dichloride
dimethylsilanediylbis(2-ethyl-1-benzindenyl)zirconium dichloride
dimethylsilanediylbis(2-propyl-1-benzindenyl)zirconium dichloride
dimethylsilanediylbis(2-butyl-1-benzindenyl)zirconium dichloride
dimethylsilanediylbis(2-i-propyl-1-benzindenyl)zirconium dichloride
dimethylsilanediylbis(2-t-butyl-1-benzindenyl)zirconium dichloride
dimethylsilanediylbis(2-trimethylsilyl-1-benzindenyl)zirconium dichloride
dimethylsilanediylbis(2-phenyl-1-benzindenyl)zirconium dichloride
dimethylsilanediylbis(2-methyl-4-phenyl-1-indenyl)zirconium dichloride
dimethylsilanediylbis(2-ethyl-4-phenyl-1-indenyl)zirconium dichloride
dimethylsilanediylbis(2-propyl-4-phenyl-1-indenyl)zirconium dichloride
dimethylsilanediylbis(2-butyl-4-phenyl-1-indenyl)zirconium dichloride
dimethylsilanediylbis(2-i-propyl-4-phenyl-1-indenyl)zirconium dichloride
dimethylsilanediylbis(2-t-butyl-4-phenyl-1-indenyl)zirconium dichloride
dimethylsilanediylbis(2-trimethylsilyl-4-phenyl-1-indenyl)zirconium dichloride
dimethylsilanediylbis(2-phenyl-4-phenyl-1-indenyl)zirconium dichloride
dimethylsilanediylbis(2-methyl-4-naphthyl-1-indenyl)zirconium dichloride
dimethylsilanediylbis(2-ethyl-4-naphthyl-1-indenyl)zirconium dichloride
dimethylsilanediylbis(2-propyl-4-naphthyl-1-indenyl)zirconium dichloride
dimethylsilanediylbis(2-butyl-4-naphthyl-1-indenyl)zirconium dichloride
dimethylsilanediylbis(2-i-propyl-4-naphthyl-1-indenyl)zirconium dichloride
dimethylsilanediylbis(2-t-butyl-4-naphthyl-1-indenyl)zirconium dichloride dimethylsilanediylbis(2-trimethylsilyl-4-naphthyl-1-indenyl)zirconium dichloride
dimethylsilanediylbis(2-phenyl-4-naphthyl-1-indenyl)zirconium dichloride
dimethylsilanediylbis(2-methyl-4-methyl-1-cyclopentadienyl)titanium dichloride
dimethylsilanediylbis(2-methyl-4-ethyl-1-cyclopentadienyl)titanium dichloride
dimethylsilanediylbis(2-methyl-4-propyl-1-cyclopentadienyl)titanium dichloride
dimethylsilanediylbis(2-methyl-4-butyl-1-cyclopentadienyl)titanium dichloride
dimethylsilanediylbis(2-methyl-4-i-propyl-1-cyclopentadienyl)titanium dichloride
dimethylsilanediylbis(2-methyl-4-i-butyl-1-cyclopentadienyl)titanium dichloride
dimethylsilanediylbis(2-methyl-4-t-butyl-1-cyclopentadienyl)titanium dichloride
dimethylsilanediylbis(2-methyl-4-trimethylsilyl-1-cyclopentadienyl)titanium dichloride dimethylsilanediylbis(2-methyl-4-phenyl-1-cyclopentadienyl)titanium dichloride
dimethylsilanediylbis(2-ethyl-4-methyl-1-cyclopentadienyl)titanium dichloride
dimethylsilanediylbis(2-ethyl-4-ethyl-1-cyclopentadienyl)titanium dichloride
dimethylsilanediylbis(2-ethyl-4-propyl-1-cyclopentadienyl)titanium dichloride
dimethylsilanediylbis(2-ethyl-4-butyl-1-cyclopentadienyl)titanium dichloride
dimethylsilanediylbis(2-ethyl-4-i-propyl-1-cyclopentadienyl)titanium dichloride
dimethylsilanediylbis(2-ethyl-4-i-butyl-1-cyclopentadienyl)titanium dichloride
dimethylsilanediylbis(2-ethyl-4-t-butyl-1-cyclopentadienyl)titanium dichloride
dimethylsilanediylbis(2-ethyl-4-trimethylsilyl-1-cyclopentadienyl)titanium dichloride
dimethylsilanediylbis(2-ethyl-4-phenyl-1-cyclopentadienyl)titanium dichloride
dimethylsilanediylbis(2-propyl-4-methyl-1-cyclopentadienyl)titanium dichloride
dimethylsilanediylbis(2-propyl-4-ethyl-1-cyclopentadienyl)titanium dichloride
dimethylsilanediylbis(2-propyl-4-propyl-1-cyclopentadienyl)titanium dichloride
dimethylsilanediylbis(2-propyl-4-butyl-1-cyclopentadienyl)titanium dichloride
dimethylsilanediylbis(2-propyl-4-i-propyl-1-cyclopentadienyl)titanium dichloride
dimethylsilanediylbis(2-propyl-4-i-butyl-1-cyclopentadienyl)titanium dichloride
dimethylsilanediylbis(2-propyl-4-t-butyl-1-cyclopentadienyl)titanium dichloride
dimethylsilanediylbis(2-propyl-4-trimethylsilyl-1-cyclopentadienyl)titanium dichloride
dimethylsilanediylbis(2-propyl-4-phenyl-1-cyclopentadienyl)titanium dichloride
dimethylsilanediylbis(2-butyl-4-methyl-1-cyclopentadienyl)titanium dichloride
dimethylsilanediylbis(2-butyl-4-ethyl-1-cyclopentadienyl)titanium dichloride
dimethylsilanediylbis(2-butyl-4-propyl-1-cyclopentadienyl)titanium dichloride
dimethylsilanediylbis(2-butyl-4-butyl-1-cyclopentadienyl)titanium dichloride
dimethylsilanediylbis(2-butyl-4-i-propyl-1-cyclopentadienyl)titanium dichloride
dimethylsilanediylbis(2-butyl-4-i-butyl-1-cyclopentadienyl)titanium dichloride
dimethylsilanediylbis(2-butyl-4-t-butyl-1-cyclopentadienyl)titanium dichloride
dimethylsilanediylbis(2-butyl-4-trimethylsilyl-1-cyclopentadienyl)titanium dichloride
dimethylsilanediylbis(2-butyl-4-phenyl-1-cyclopentadienyl)titanium dichloride
dimethylsilanediylbis(2-i-propyl-4-methyl-1-cyclopentadienyl)titanium dichloride
dimethylsilanediylbis(2-i-propyl-4-ethyl-1-cyclopentadienyl)titanium dichloride
dimethylsilanediylbis(2-i-propyl-4-propyl-1-cyclopentadienyl)titanium dichloride
dimethylsilanediylbis(2-i-propyl-4-butyl-1-cyclopentadienyl)titanium dichloride
dimethylsilanediylbis(2-i-propyl-4-i-propyl-1-cyclopentadienyl)titanium dichloride
dimethylsilanediylbis(2-i-propyl-4-i-butyl-1-cyclopentadienyl)titanium dichloride
dimethylsilanediylbis(2-i-propyl-4-t-butyl-1-cyclopentadienyl)titanium dichloride
dimethylsilanediylbis(2-i-propyl-4-trimethylsilyl-1-cyclopentadienyl)titanium dichloride
dimethylsilanediylbis(2-i-propyl-4-phenyl-1-cyclopentadienyl)titanium dichloride
dimethylsilanediylbis(2-t-butyl-4-methyl-1-cyclopentadienyl)titanium dichloride
dimethylsilanediylbis(2-t-butyl-4-ethyl-1-cyclopentadienyl)titanium dichloride
dimethylsilanediylbis(2-t-butyl-4-propyl-1-cyclopentadienyl)titanium dichloride
dimethylsilanediylbis(2-t-butyl-4-butyl-1-cyclopentadienyl)titanium dichloride
dimethylsilanediylbis(2-t-butyl-4-i-propyl-1-cyclopentadienyl)titanium dichloride
dimethylsilanediylbis(2-t-butyl-4-i-butyl-1-cyclopentadienyl)titanium dichloride
dimethylsilanediylbis(2-t-butyl-4-t-butyl-1-cyclopentadienyl)titanium dichloride
dimethylsilanediylbis(2-t-butyl-4-trimethylsilyl-1-cyclopentadienyl)titanium dichloride
dimethylsilanediylbis(2-t-butyl-4-phenyl-1-cyclopentadienyl)titanium dichloride
dimethylsilanediylbis(2-trimethylsilyl-4-methyl-1-cyclopentadienyl)titanium dichloride
dimethylsilanediylbis(2-trimethylsilyl-4-ethyl-1-cyclopentadienyl)titanium dichloride
dimethylsilanediylbis(2-trimethylsilyl-4-propyl-1-cyclopentadienyl)titanium dichloride
dimethylsilanediylbis(2-trimethylsilyl-4-butyl-1-cyclopentadienyl)titanium dichloride
dimethylsilanediylbis(2-trimethylsilyl-4-i-propyl-1-cyclopentadienyl)titanium dichloride
dimethylsilanediylbis(2-trimethylsilyl-4-i-butyl-1-cyclopentadienyl)titanium dichloride
dimethylsilanediylbis(2-trimethylsilyl-4-t-butyl-1-cyclopentadienyl)titanium dichloride
dimethylsilanediylbis(2-trimethylsilyl-4-trimethylsilyl-1-cyclopentadienyl)titanium dichloride
dimethylsilanediylbis(2-trimethylsilyl-4-phenyl-1-cyclopentadienyl)titanium dichloride
dimethylsilanediylbis(2-phenyl-4-methyl-1-cyclopentadienyl)titanium dichloride
dimethylsilanediylbis(2-phenyl-4-ethyl-1-cyclopentadienyl)titanium dichloride
dimethylsilanediylbis(2-phenyl-4-propyl-1-cyclopentadienyl)titanium dichloride
dimethylsilanediylbis(2-phenyl-4-butyl-1-cyclopentadienyl)titanium dichloride
dimethylsilanediylbis(2-phenyl-4-i-propyl-1-cyclopentadienyl)titanium dichloride
dimethylsilanediylbis(2-phenyl-4-i-butyl-1-cyclopentadienyl)titanium dichloride
dimethylsilanediylbis(2-phenyl-4-t-butyl-1-cyclopentadienyl)titanium dichloride
dimethylsilanediylbis(2-phenyl-4-trimethylsilyl-1-cyclopentadienyl)titanium dichloride
dimethylsilanediylbis(2-phenyl-4-phenyl-1-cyclopentadienyl)titanium dichloride
dimethylsilanediylbis(2-methyl-1-indenyl)titanium dichloride
dimethylsilanediylbis(2-ethyl-1-indenyl)titanium dichloride
dimethylsilanediylbis(2-propyl-1-indenyl)titanium dichloride
dimethylsilanediylbis(2-butyl-1-indenyl)titanium dichloride dimethylsilanediylbis(2-i-propyl-1-indenyl)titanium dichloride
dimethylsilanediylbis(2-t-butyl-1-indenyl)titanium dichloride
dimethylsilanediylbis(2-trimethylsilyl-1-indenyl)titanium dichloride
dimethylsilanediylbis(2-phenyl-1-indenyl)titanium dichloride
dimethylsilanediylbis(2-methyl-4,5,6,7-tetrahydro-1-indenyl)titanium dichloride
dimethylsilanediylbis(2-ethyl-4,5,6,7-tetrahydro-1-indenyl)titanium dichloride
dimethylsilanediylbis(2-propyl-4,5,6,7-tetrahydro-1-indenyl)titanium dichloride
dimethylsilanediylbis(2-butyl-4,5,6,7-tetrahydro-1-indenyl)titanium dichloride
dimethylsilanediylbis(2-i-propyl-4,5,6,7-tetrahydro-1-indenyl)titanium dichloride
dimethylsilanediylbis(2-t-butyl-4,5,6,7-tetrahydro-1-indenyl)titanium dichloride
dimethylsilanediylbis(2-trimethylsilyl-4,5,6,7-tetrahydro-1-indenyl)titanium dichloride
dimethylsilanediylbis(2-phenyl-4,5,6,7-tetrahydro-1-indenyl)titanium dichloride
dimethylsilanediylbis(2-methyl-4,7-dimethyl-1-indenyl)titanium dichloride
dimethylsilanediylbis(2-ethyl-4,7-dimethyl-1-indenyl)titanium dichloride
dimethylsilanediylbis(2-propyl-4,7-dimethyl-1-indenyl)titanium dichloride
dimethylsilanediylbis(2-butyl-4,7-dimethyl-1-indenyl)titanium dichloride
dimethylsilanediylbis(2-i-propyl-4,7-dimethyl-1-indenyl)titanium dichloride
dimethylsilanediylbis(2-t-butyl-4,7-dimethyl-1-indenyl)titanium dichloride
dimethylsilanediylbis(2-trimethylsilyl-4,7-dimethyl-1-indenyl)titanium dichloride
dimethylsilanediylbis(2-phenyl-4,7-dimethyl-1-indenyl)titanium dichloride
dimethylsilanediylbis(2-methyl-4,6-di-i-propyl-1-indenyl)titanium dichloride
dimethylsilanediylbis(2-ethyl-4,6-di-i-propyl-1-indenyl)titanium dichloride
dimethylsilanediylbis(2-propyl-4,6-di-i-propyl-1-indenyl)titanium dichloride
dimethylsilanediylbis(2-butyl-4,6-di-i-propyl-1-indenyl)titanium dichloride
dimethylsilanediylbis(2-i-propyl-4,6-di-i-propyl-1-indenyl)titanium dichloride
dimethylsilanediylbis(2-t-butyl-4,6-di-i-propyl-1-indenyl)titanium dichloride
dimethylsilanediylbis(2-trimethylsilyl-4,6-di-i-propyl-1-indenyl)titanium dichloride
dimethylsilanediylbis(2-phenyl-4,6-di-i-propyl-1-indenyl)titanium dichloride
dimethylsilanediylbis(2-methyl-1-benzindenyl)titanium dichloride
dimethylsilanediylbis(2-ethyl-1-benzindenyl)titanium dichloride
dimethylsilanediylbis(2-propyl-1-benzindenyl)titanium dichloride
dimethylsilanediylbis(2-butyl-1-benzindenyl)titanium dichloride
dimethylsilanediylbis(2-i-propyl-1-benzindenyl)titanium dichloride
dimethylsilanediylbis(2-t-butyl-1-benzindenyl)titanium dichloride
dimethylsilanediylbis(2-trimethylsilyl-1-benzindenyl)titanium dichloride
dimethylsilanediylbis(2-phenyl-1-benzindenyl)titanium dichloride
dimethylsilanediylbis(2-methyl-4-phenyl-1-indenyl)titanium dichloride
dimethylsilanediylbis(2-ethyl-4-phenyl-1-indenyl)titanium dichloride
dimethylsilanediylbis(2-propyl-4-phenyl-1-indenyl)titanium dichloride
dimethylsilanediylbis(2-butyl-4-phenyl-1-indenyl)titanium dichloride
dimethylsilanediylbis(2-i-propyl-4-phenyl-1-indenyl)titanium dichloride
dimethylsilanediylbis(2-t-butyl-4-phenyl-1-indenyl)titanium dichloride
dimethylsilanediylbis(2-trimethylsilyl-4-phenyl-1-indenyl)titanium dichloride
dimethylsilanediylbis(2-phenyl-4-phenyl-1-indenyl)titanium dichloride
dimethylsilanediylbis(2-methyl-4-naphthyl-1-indenyl)titanium dichloride
dimethylsilanediylbis(2-ethyl-4-naphthyl-1-indenyl)titanium dichloride
dimethylsilanediylbis(2-propyl-4-naphthyl-1-indenyl)titanium dichloride
dimethylsilanediylbis(2-butyl-4-naphthyl-1-indenyl)titanium dichloride
dimethylsilanediylbis(2-i-propyl-4-naphthyl-1-indenyl)titanium dichloride
dimethylsilanediylbis(2-t-butyl-4-naphthyl-1-indenyl)titanium dichloride
dimethylsilanediylbis(2-trimethylsilyl-4-naphthyl-1-indenyl)titanium dichloride
dimethylsilanediylbis(2-phenyl-4-naphthyl-1-indenyl)titanium dichloride
dimethylsilanediylbis(2-methyl-4-methyl-1-cyclopentadienyl)hafnium dichloride
dimethylsilanediylbis(2-methyl-4-ethyl-1-cyclopentadienyl)hafnium dichloride
dimethylsilanediylbis(2-methyl-4-propyl-1-cyclopentadienyl)hafnium dichloride
dimethylsilanediylbis(2-methyl-4-butyl-1-cyclopentadienyl)hafnium dichloride
dimethylsilanediylbis(2-methyl-4-i-propyl-1-cyclopentadienyl)hafnium dichloride
dimethylsilanediylbis(2-methyl-4-i-butyl-1-cyclopentadienyl)hafnium dichloride
dimethylsilanediylbis(2-methyl-4-t-butyl-1-cyclopentadienyl)hafnium dichloride
dimethylsilanediylbis(2-methyl-4-trimethylsilyl-1-cyclopentadienyl)hafnium dichloride
dimethylsilanediylbis(2-methyl-4-phenyl-1-cyclopentadienyl)hafnium dichloride
dimethylsilanediylbis(2-ethyl-4-methyl-1-cyclopentadienyl)hafnium dichloride
dimethylsilanediylbis(2-ethyl-4-ethyl-1-cyclopentadienyl)hafnium dichloride
dimethylsilanediylbis(2-ethyl-4-propyl-1-cyclopentadienyl)hafnium dichloride
dimethylsilanediylbis(2-ethyl-4-butyl-1-cyclopentadienyl)hafnium dichloride
dimethylsilanediylbis(2-ethyl-4-i-propyl-1-cyclopentadienyl)hafnium dichloride
dimethylsilanediylbis(2-ethyl-4-i-butyl-1-cyclopentadienyl)hafnium dichloride
dimethylsilanediylbis(2-ethyl-4-t-butyl-1-cyclopentadienyl)hafnium dichloride dimethylsilanediylbis(2-ethyl-4-trimethylsilyl-1-cyclopentadienyl)hafnium dichloride
dimethylsilanediylbis(2-ethyl-4-phenyl-1-cyclopentadienyl)hafnium dichloride
dimethylsilanediylbis(2-propyl-4-methyl-1-cyclopentadienyl)hafnium dichloride
dimethylsilanediylbis(2-propyl-4-ethyl-1-cyclopentadienyl)hafnium dichloride
dimethylsilanediylbis(2-propyl-4-propyl-1-cyclopentadienyl)hafnium dichloride
dimethylsilanediylbis(2-propyl-4-butyl-1-cyclopentadienyl)hafnium dichloride
dimethylsilanediylbis(2-propyl-4-i-propyl-1-cyclopentadienyl)hafnium dichloride
dimethylsilanediylbis(2-propyl-4-i-butyl-1-cyclopentadienyl)hafnium dichloride
dimethylsilanediylbis(2-propyl-4-t-butyl-1-cyclopentadienyl)hafnium dichloride
dimethylsilanediylbis(2-propyl-4-trimethylsilyl-1-cyclopentadienyl)hafnium dichloride
dimethylsilanediylbis(2-propyl-4-phenyl-1-cyclopentadienyl)hafnium dichloride
dimethylsilanediylbis(2-butyl-4-methyl-1-cyclopentadienyl)hafnium dichloride
dimethylsilanediylbis(2-butyl-4-ethyl-1-cyclopentadienyl)hafnium dichloride
dimethylsilanediylbis(2-butyl-4-propyl-1-cyclopentadienyl)hafnium dichloride
dimethylsilanediylbis(2-butyl-4-butyl-1-cyclopentadienyl)hafnium dichloride
dimethylsilanediylbis(2-butyl-4-i-propyl-1-cyclopentadienyl)hafnium dichloride
dimethylsilanediylbis(2-butyl-4-i-butyl-1-cyclopentadienyl)hafnium dichloride
dimethylsilanediylbis(2-butyl-4-t-butyl-1-cyclopentadienyl)hafnium dichloride
dimethylsilanediylbis(2-butyl-4-trimethylsilyl-1-cyclopentadienyl)hafnium dichloride
dimethylsilanediylbis(2-butyl-4-phenyl-1-cyclopentadienyl)hafnium dichloride
dimethylsilanediylbis(2-i-propyl-4-methyl-1-cyclopentadienyl)hafnium dichloride
dimethylsilanediylbis(2-i-propyl-4-ethyl-1-cyclopentadienyl)hafnium dichloride
dimethylsilanediylbis(2-i-propyl-4-propyl-1-cyclopentadienyl)hafnium dichloride
dimethylsilanediylbis(2-i-propyl-4-butyl-1-cyclopentadienyl)hafnium dichloride
dimethylsilanediylbis(2-i-propyl-4-i-propyl-1-cyclopentadienyl)hafnium dichloride
dimethylsilanediylbis(2-i-propyl-4-i-butyl-1-cyclopentadienyl)hafnium dichloride
dimethylsilanediylbis(2-i-propyl-4-t-butyl-1-cyclopentadienyl)hafnium dichloride
dimethylsilanediylbis(2-i-propyl-4-trimethylsilyl-1-cyclopentadienyl)hafnium dichloride
dimethylsilanediylbis(2-i-propyl-4-phenyl-1-cyclopentadienyl)hafnium dichloride
dimethylsilanediylbis(2-t-butyl-4-methyl-1-cyclopentadienyl)hafnium dichloride
dimethylsilanediylbis(2-t-butyl-4-ethyl-1-cyclopentadienyl)hafnium dichloride
dimethylsilanediylbis(2-t-butyl-4-propyl-1-cyclopentadienyl)hafnium dichloride
dimethylsilanediylbis(2-t-butyl-4-butyl-1-cyclopentadienyl)hafnium dichloride
dimethylsilanediylbis(2-t-butyl-4-i-propyl-1-cyclopentadienyl)hafnium dichloride
dimethylsilanediylbis(2-t-butyl-4-i-butyl-1-cyclopentadienyl)hafnium dichloride
dimethylsilanediylbis(2-t-butyl-4-t-butyl-1-cyclopentadienyl)hafnium dichloride
dimethylsilanediylbis(2-t-butyl-4-trimethylsilyl-1-cyclopentadienyl)hafnium dichloride
dimethylsilanediylbis(2-t-butyl-4-phenyl-1-cyclopentadienyl)hafnium dichloride
dimethylsilanediylbis(2-trimethylsilyl-4-methyl-1-cyclopentadienyl)hafnium dichloride
dimethylsilanediylbis(2-trimethylsilyl-4-ethyl-1-cyclopentadienyl)hafnium dichloride
dimethylsilanediylbis(2-trimethylsilyl-4-propyl-1-cyclopentadienyl)hafnium dichloride
dimethylsilanediylbis(2-trimethylsilyl-4-butyl-1-cyclopentadienyl)hafnium dichloride
dimethylsilanediylbis(2-trimethylsilyl-4-i-propyl-1-cyclopentadienyl)hafnium dichloride
dimethylsilanediylbis(2-trimethylsilyl-4-i-butyl-1-cyclopentadienyl)hafnium dichloride
dimethylsilanediylbis(2-trimethylsilyl-4-t-butyl-1-cyclopentadienyl)hafnium dichloride
dimethylsilanediylbis(2-trimethylsilyl-4-trimethylsilyl-1-cyclopentadienyl)hafnium dichloride
dimethylsilanediylbis(2-trimethylsilyl-4-phenyl-1-cyclopentadienyl)hafnium dichloride
dimethylsilanediylbis(2-phenyl-4-methyl-1-cyclopentadienyl)hafnium dichloride
dimethylsilanediylbis(2-phenyl-4-ethyl-1-cyclopentadienyl)hafnium dichloride
dimethylsilanediylbis(2-phenyl-4-propyl-1-cyclopentadienyl)hafnium dichloride
dimethylsilanediylbis(2-phenyl-4-butyl-1-cyclopentadienyl)hafnium dichloride
dimethylsilanediylbis(2-phenyl-4-i-propyl-1-cyclopentadienyl)hafnium dichloride
dimethylsilanediylbis(2-phenyl-4-i-butyl-1-cyclopentadienyl)hafnium dichloride
dimethylsilanediylbis(2-phenyl-4-t-butyl-1-cyclopentadienyl)hafnium dichloride
dimethylsilanediylbis(2-phenyl-4-trimethylsilyl-1-cyclopentadienyl)hafnium dichloride
dimethylsilanediylbis(2-phenyl-4-phenyl-1-cyclopentadienyl)hafnium dichloride
dimethylsilanediylbis(2-methyl-1-indenyl)hafnium dichloride
dimethylsilanediylbis(2-ethyl-1-indenyl)hafnium dichloride
dimethylsilanediylbis(2-propyl-1-indenyl)hafnium dichloride
dimethylsilanediylbis(2-butyl-1-indenyl)hafnium dichloride
dimethylsilanediylbis(2-i-propyl-1-indenyl)hafnium dichloride
dimethylsilanediylbis(2-t-butyl-1-indenyl)hafnium dichloride
dimethylsilanediylbis(2-trimethylsilyl-1-indenyl)hafnium dichloride
dimethylsilanediylbis(2-phenyl-1-indenyl)hafnium dichloride
dimethylsilanediylbis(2-methyl-4,5,6,7-tetrahydro-1-indenyl)hafnium dichloride
dimethylsilanediylbis(2-ethyl-4,5,6,7-tetrahydro-1-indenyl)hafnium dichloride
dimethylsilanediylbis(2-propyl-4,5,6,7-tetrahydro-1-indenyl)hafnium dichloride
dimethylsilanediylbis(2-butyl-4,5,6,7-tetrahydro-1-indenyl)hafnium dichloride dimethylsilanediylbis(2-i-propyl-4,5,6,7-tetrahydro-1-indenyl)hafnium dichloride
dimethylsilanediylbis(2-t-butyl-4,5,6,7-tetrahydro-1-indenyl)hafnium dichloride
dimethylsilanediylbis(2-trimethylsilyl-4,5,6,7-tetrahydro-1-indenyl)hafnium dichloride
dimethylsilanediylbis(2-phenyl-4,5,6,7-tetrahydro-1-indenyl)hafnium dichloride
dimethylsilanediylbis(2-methyl-4,7-dimethyl-1-indenyl)hafnium dichloride
dimethylsilanediylbis(2-ethyl-4,7-dimethyl-1-indenyl)hafnium dichloride
dimethylsilanediylbis(2-propyl-4,7-dimethyl-1-indenyl)hafnium dichloride
dimethylsilanediylbis(2-butyl-4,7-dimethyl-1-indenyl)hafnium dichloride
dimethylsilanediylbis(2-i-propyl-4,7-dimethyl-1-indenyl)hafnium dichloride
dimethylsilanediylbis(2-t-butyl-4,7-dimethyl-1-indenyl)hafnium dichloride
dimethylsilanediylbis(2-trimethylsilyl-4,7-dimethyl-1-indenyl)hafnium dichloride
dimethylsilanediylbis(2-phenyl-4,7-dimethyl-1-indenyl)hafnium dichloride
dimethylsilanediylbis(2-methyl-4,6-di-i-propyl-1-indenyl)hafnium dichloride
dimethylsilanediylbis(2-ethyl-4,6-di-i-propyl-1-indenyl)hafnium dichloride
dimethylsilanediylbis(2-propyl-4,6-di-i-propyl-1-indenyl)hafnium dichloride
dimethylsilanediylbis(2-butyl-4,6-di-i-propyl-1-indenyl)hafnium dichloride
dimethylsilanediylbis(2-i-propyl-4,6-di-i-propyl-1-indenyl)hafnium dichloride
dimethylsilanediylbis(2-t-butyl-4,6-di-i-propyl-1-indenyl)hafnium dichloride
dimethylsilanediylbis(2-trimethylsilyl-4,6-di-i-propyl-1-indenyl)hafnium dichloride
dimethylsilanediylbis(2-phenyl-4,6-di-i-propyl-1-indenyl)hafnium dichloride
dimethylsilanediylbis(2-methyl-1-benzindenyl)hafnium dichloride
dimethylsilanediylbis(2-ethyl-1-benzindenyl)hafnium dichloride
dimethylsilanediylbis(2-propyl-1-benzindenyl)hafnium dichloride
dimethylsilanediylbis(2-butyl-1-benzindenyl)hafnium dichloride
dimethylsilanediylbis(2-i-propyl-1-benzindenyl)hafnium dichloride
dimethylsilanediylbis(2-t-butyl-1-benzindenyl)hafnium dichloride
dimethylsilanediylbis(2-trimethylsilyl-1-benzindenyl)hafnium dichloride
dimethylsilanediylbis(2-phenyl-1-benzindenyl)hafnium dichloride
dimethylsilanediylbis(2-methyl-4-phenyl-1-indenyl)hafnium dichloride
dimethylsilanediylbis(2-ethyl-4-phenyl-1-indenyl)hafnium dichloride
dimethylsilanediylbis(2-propyl-4-phenyl-1-indenyl)hafnium dichloride
dimethylsilanediylbis(2-butyl-4-phenyl-1-indenyl)hafnium dichloride
dimethylsilanediylbis(2-i-propyl-4-phenyl-1-indenyl)hafnium dichloride
dimethylsilanediylbis(2-t-butyl-4-phenyl-1-indenyl)hafnium dichloride
dimethylsilanediylbis(2-trimethylsilyl-4-phenyl-1-indenyl)hafnium dichloride
dimethylsilanediylbis(2-phenyl-4-phenyl-1-indenyl)hafnium dichloride
dimethylsilanediylbis(2-methyl-4-naphthyl-1-indenyl)hafnium dichloride
dimethylsilanediylbis(2-ethyl-4-naphthyl-1-indenyl)hafnium dichloride
dimethylsilanediylbis(2-propyl-4-naphthyl-1-indenyl)hafnium dichloride
dimethylsilanediylbis(2-butyl-4-naphthyl-1-indenyl)hafnium dichloride
dimethylsilanediylbis(2-i-propyl-4-naphthyl-1-indenyl)hafnium dichloride
dimethylsilanediylbis(2-t-butyl-4-naphthyl-1-indenyl)hafnium dichloride
dimethylsilanediylbis(2-trimethylsilyl-4-naphthyl-1-indenyl)hafnium dichloride
dimethylsilanediylbis(2-phenyl-4-naphthyl-1-indenyl)hafnium dichloride and also the analogous diphenylsilylene-bridged complexes.

Such complexes can be synthesized by methods known per se, with preference being given to reacting the appropriately substituted cyclic hydrocarbon anions with halides of titanium, zirconium, hafnium, vanadium, niobium or tantalum. Examples of corresponding preparative methods are described, for example, in Brintzinger et al., Journal of Organometallic Chemistry, 369 (1989), p. 359–370.

The ansa-metallocene complexes prepared by these customary methods are usually obtained in an rac:meso ratio of about 1:1.

In the process of the present invention, the photochemical conversion can be carried out by electromagnetically irradiating the meso form, the racemate or the mixture of rac and meso forms with a wavelength of less than 1000 nm, preferably from 50 to 500 nm, for example using a UV lamp. It has been found to be useful to carry out the irradiation at from −80° C. to +100° C. over a period of from 0.01 to 72 hours.

According to the present invention, the photochemical conversion is carried out in the presence of an enantiomerically pure auxiliary reagent. Particularly suitable enantiomerically pure auxiliary reagents are those which are bifunctional, in particular dialkoxides.

Particularly useful dialkoxides are those which are derived from dialcohols of the formula II

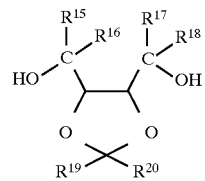

where the substituents have the following meanings:

$R^{15}$ to $R^{18}$ are hydrogen, $C_1$–$C_{10}$-alkyl or $C_6$–$C_{15}$-aryl,
$R^{19}$ and $R^{20}$ are hydrogen, $C_1$–$C_{10}$-alkyl, $C_3$–$C_{10}$-cycloalkyl or $C_6$–$C_{15}$-aryl, or $R^{19}$ and $R^{20}$ together form a $C_3$–$C_{10}$-cycloalkyl ring or from

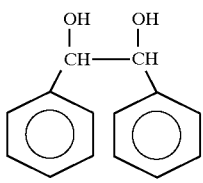

or from

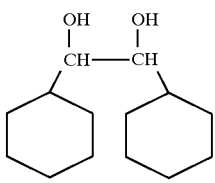

or, particularly preferably from binaphthols, in particular from 1,1'-bi-2-naphthol

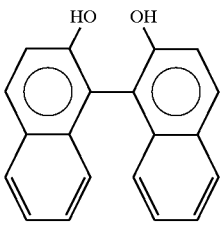

The enantiomerically pure dialcohols are known per se and are commercially available. These dialcohols are then subjected to a simple reaction with a suitable base such as n-butyllithium to form the enantiomerically pure dialkoxide which is then used as enantiomerically pure auxiliary reagent. Of course, other enantiomerically pure compounds such as dimercaptans or diamines are also suitable as enantiomerically pure auxiliary reagents. These compounds and also methods of preparing them are likewise known per se.

Mixtures of various enantiomerically pure auxiliary reagents can likewise be used.

The molar ratio of enantiomerically pure auxiliary reagent to the ansa-metallocene complex is preferably from 0.1:1 to 10:1, in particular from 0.5:1 to 1.5:1.

It has been found to be particularly useful to carry out the reaction in the presence of a solvent. Preference is given to using organic solvents such as tetrahydrofuran, $CH_2Cl_2$, $CHCl_3$ and, in particular, aromatic hydrocarbons such as benzene and toluene. It is also possible to use solvent mixtures.

The following process has been found to be particularly useful: a mixture of rac and meso forms of an ansa-metallocene complex or only the meso form or only the racemate of an ansa-metallocene complex, the enantiomerically pure auxiliary reagent and the solvent are placed in an irradiation vessel of a UV irradiation apparatus, preferably under an inert gas atmosphere. The enantiomerically pure auxiliary reagent then reacts during the irradiation with only one enantiomerically pure form of the ansa-metallocene complex to form a photoinactive product, while the meso form and the other enantiomerically pure form are isomerized. The photoinactive product can then be converted into the corresponding dichloride of the ansa-metallocene complex by methods known per se, as described in Brintzinger et al., Journal of Organometallic Chemistry, 232 (1982), p. 233–247, by reaction with, for example, methyllithium and subsequent cleavage using gaseous HCl.

As an alternative, the alkoxide can also, as described in JP-A 05287017, be alkylated by reaction with a metal alkyl and activated in situ with a cation former to give the polymerization-active metallocenium cation. In the preferred use of ansa-metallocene complexes as catalysts, it is also possible to use the photoinactive product (for example metallocene binaphthoxide), directly with customary cocatalysts, such as aluminoxanes, as active catalyst components, as described in Waymouth et al., J. Am. Chem. Soc., 112 (1990), p.4911–4914.

The process of the present invention gives quantitative conversion of the meso form or the racemate of an ansa-metallocene complex or a mixture thereof into one of its enantiomers, with the process being simple in process terms and inexpensive. The enantiomerically pure form of an ansa-metallocene complex is employed in particular as catalyst in organic synthesis.

EXAMPLES

The photochemical conversion was carried out by irradiation with a Phillips HPK 125 W mercury vapor lamp.

Example 1

Preparation of enantiomerically pure dimethylsilanediylbis(2-methyl-4-tert-butyl-1-cyclopentadienyl)zirconium 1,1'-bi-2-naphthoxide by conversion of an rac/meso mixture.

49 mg (0.1 mmol) of an rac/meso mixture (molar ratio 1:1) of dimethylsilanediylbis(2-methyl-4-tert-butyl-1-cyclopentadienyl)zirconium dichloride, 37 mg (0.125 mmol) of enantiomerically pure dilithium 1,1'-bi-2-naphthoxide (prepared from R(+)-1,1'-bi-2-naphthol) and 4 ml of absolute toluene were placed in a Schlenk vessel under inert gas. Irradiation was carried out while stirring for a period of 29 hours at 40° C. The solution was subsequently decanted from the solids which had settled out and the solvent was taken off under reduced pressure. The solid residue was dissolved in 3 ml of diethyl ether and crystallized at −80° C. to give a yellow powder. The quantitative conversion to enantiomerically pure dimethylsilanediylbis (2-methyl-4-tertbutyl-1-cyclopentadienyl)zirconium 1,1'-bi-2-naphthoxide could be confirmed by measurement of the specific rotation.

Dilithium R(+)-1,1'bi-2-naphthoxide:

$[\alpha]_{589}=-618°$ (c=1, tetrahydrofuran)

Dimethylsilanediylbis(2-methyl-4-tert-butyl-1-cyclopentadienyl)zirconium 1,1'-bi-2-naphthoxide:

$[\alpha]_{589}=-780°$ (c=1, toluene)

$[\alpha]_{436}=-2620°$ (c=1, toluene)

Example 2

Preparation of enantiomerically pure dimethylsilanediylbis(2-methyl-4-phenyl-1-cyclopentadienyl)zirconium 1,1'-bi-2-naphthoxide by conversion of the meso form 53 mg (0.1 mmol) of meso-dimethylsilanediylbis(2-methyl-4-phenyl-1-cyclopentadienyl)zirconium dichloride, 37 mg (1.125 mmol) of dilithium 1,1'-bi-2-naphthoxide and 5 ml of absolute toluene were placed in a Schlenk vessel under an inert gas atmosphere. Irradiation was carried out while stirring over a period of 5 hours at 40° C. The solution was subsequently decanted from the solids which had settled out and the solvent was taken off under reduced pressure. The solid residue was washed with pentane and dried under reduced pressure. This gave 65.5 mg (=88 %) of enantiomerically pure dimethylsilanediylbis(2-methyl-4-phenyl-1-cyclopentadienyl)zirconium 1,1'-bi-2-naphthoxide.

Dilithium R(+)-1,1'-bi-2-naphthoxide:

$[\alpha]_{589}=-618°$ (c=1, tetrahydrofuran)

Dimethylsilanediylbis(2-methyl-4-phenyl-1-cyclopentadienyl)zirconium 1,1'-bi-2-naphthoxide:

$[\alpha]_{589}=-750°$ (c=0.05, toluene)

$[\alpha]_{436}=-2100°$ (c=0.05, toluene)

We claim:

1. A process for converting the achiral meso form or the racemate of an ansa-metallocene complex or a mixture thereof into one of its enantiomers, which comprises carrying out the conversion photochemically in the presence of an enantiomerically pure auxiliary reagent.

2. A process as claimed in claim 1, wherein the conversion is carried out in the presence of an organic solvent.

3. A process as claimed in claim 1, wherein the photochemical conversion is carried out using electromagnetic radiation having a wavelength of less than 1000 nm.

4. A process as claimed in claim 1, wherein the enantiomerically pure auxiliary reagent is bifunctional.

5. A process as claimed in claim 1, wherein the enantiomerically pure auxiliary reagent used is a dialkoxide.

6. A process as claimed in claim 1, wherein the enantiomerically pure auxiliary reagent used is an enantiomer of a binaphthoxide.

7. A process as claimed in claim 1, wherein the ansa-metallocene complexes used have the formula I

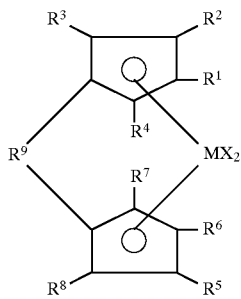

where the substituents and indices have the following meanings:

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^{10}$, where $R^{10}$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, $R^1$ to $R^8$ are hydrogen, $C_1$–$C_{10}$-alkyl, 5- to 7-membered cycloalkyl which may in turn bear a $C_1$–$C_{10}$-alkyl group as substituent, $C_6$–$Cl_5$-aryl or arylalkyl, where two adjacent radicals may also together form a cyclic group having from 4 to 15 carbon atoms, or $Si(R^{11})_3$ where $R^{11}$ is $C_1$–$C_{10}$-alkyl, $C_6$–$C_{15}$-aryl or $C_3$–$C_{10}$-cycloalkyl, $R^9$ is

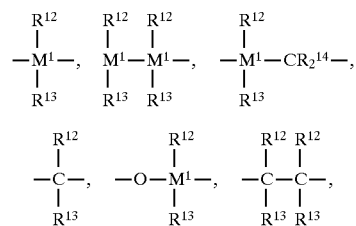

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$ where $R^{12}$, $R^{13}$ and $R^{14}$ are identical or different and are hydrogen, halogen, $C_1$–$C_{10}$-alkyl, $C_1$–$C_{10}$-fluoroalkyl, $C_6$–$C_{10}$-fluoroaryl, $C_6$–$C_{10}$-aryl, $C_1$–$C_{10}$-alkoxy, $C_2$–$C_{10}$-alkenyl, $C_7$–$C_{40}$-arylalkyl, $C_8$–$C_{40}$-arylalkenyl or $C_7$–$C_{40}$-alkylaryl or $R^{12}$ and $R^{13}$ or $R^{12}$ and $R^{14}$ in each case together with the atoms connecting them form a ring, and $M^1$ is silicon, germanium or tin.

8. A process as claimed in claim 1, wherein the ansa-metallocene complexes are substituted in the 2 position of the cyclopentadienyl rings.

9. A process as claimed in claim 1, wherein the ansa-metallocene complexes used are silyl-bridged complexes.

* * * * *

UNITED STATES PATENT AND TRADEMARK OFFICE
CERTIFICATE OF CORRECTION

PATENT NO.: 5,840,950

DATED: November 24, 1998

INVENTOR(S): FISCHER et al.

It is certified that error appears in the above-identified patent and that said Letters Patent is hereby corrected as shown below:

Col. 18, claim 7, line 11, "$C_6$-$Cl_5$-" should be -- $C_6$-$C_{15}$- --.

Signed and Sealed this

Twenty-seventh Day of April, 1999

*Attest:*

Q. TODD DICKINSON

*Attesting Officer*   Acting Commissioner of Patents and Trademarks